US011266372B2

(12) United States Patent
Thakur et al.

(10) Patent No.: US 11,266,372 B2
(45) Date of Patent: Mar. 8, 2022

(54) CHRONIC MONITORING OF BLOOD PRESSURE USING HEART SOUNDS

(71) Applicant: Cardiac Pacemakers, Inc., St. Paul, MN (US)

(72) Inventors: Pramodsingh Hirasingh Thakur, Woodbury, MN (US); Michael J. Kane, St Paul, MN (US); Jeffrey E. Stahmann, Ramsey, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 80 days.

(21) Appl. No.: 16/269,171

(22) Filed: Feb. 6, 2019

(65) Prior Publication Data
US 2019/0274655 A1 Sep. 12, 2019

Related U.S. Application Data

(60) Provisional application No. 62/639,143, filed on Mar. 6, 2018.

(51) Int. Cl.
*A61B 7/02* (2006.01)
*A61B 5/00* (2006.01)
(Continued)

(52) U.S. Cl.
CPC ............ *A61B 7/026* (2013.01); *A61B 5/0006* (2013.01); *A61B 5/021* (2013.01); *A61B 5/335* (2021.01);
(Continued)

(58) Field of Classification Search
CPC ........... A61B 7/003; A61B 7/04; A61B 7/026; A61B 5/0031; A61B 5/0205;
(Continued)

(56) References Cited

U.S. PATENT DOCUMENTS 6,869,404 B2 3/2005 Schulhauser et al.
6,942,622 B1 * 9/2005 Turcott ................ A61B 5/0002
600/485
(Continued)

FOREIGN PATENT DOCUMENTS

CN 111818852 A 10/2020
WO WO-2019173019 A1 9/2019

OTHER PUBLICATIONS

Klabunde, Richard E., "Effects of Preload, Afterload and Inotropy on Ventricular Pressure-Volume Loops", http://www.cvphysiology.com/Cardiac%20Function/CF025, Revised Dec. 15, 2017, pp. 1-4.
(Continued)

*Primary Examiner* — Michael W Kahelin
(74) *Attorney, Agent, or Firm* — Schwegman Lundberg & Woessner, P.A.

(57) ABSTRACT

This document discusses, among other things, systems and methods to determine an indication of contractility of a heart of a patient using received physiologic information, and to determine blood pressure information of the patient using the heart sound information and the determined indication of contractility of the heart. The system can include an assessment circuit configured to determine an indication of contractility of a heart of the patient using first heart sound (S1) information of the patient, and to determine blood pressure information of the patient using second heart sound (S2) information of the patient and the determined indication of contractility of the heart.

16 Claims, 5 Drawing Sheets

(51) Int. Cl.
*A61N 1/39* (2006.01)
*A61B 5/021* (2006.01)
*A61B 7/00* (2006.01)
*A61B 7/04* (2006.01)
*A61B 5/335* (2021.01)
*A61B 5/0205* (2006.01)
*A61N 1/04* (2006.01)
*A61N 1/362* (2006.01)
*A61B 5/352* (2021.01)

(52) U.S. Cl.
CPC ............ *A61B 5/7275* (2013.01); *A61B 7/003* (2013.01); *A61B 7/04* (2013.01); *A61N 1/3904* (2017.08); *A61B 5/0031* (2013.01); *A61B 5/0205* (2013.01); *A61B 5/352* (2021.01); *A61N 1/046* (2013.01); *A61N 1/362* (2013.01); *A61N 1/3925* (2013.01)

(58) Field of Classification Search
CPC ..... A61B 5/0456; A61B 5/0006; A61B 5/021; A61B 5/04325; A61B 5/7275; A61N 1/3904; A61N 1/046; A61N 1/362; A61N 1/3925
See application file for complete search history.

(56) References Cited

U.S. PATENT DOCUMENTS

| | | | |
|---|---|---|---|
| 7,972,275 B2 | 7/2011 | Siejko et al. | |
| 8,048,001 B2 | 11/2011 | Patangay et al. | |
| 8,801,624 B2* | 8/2014 | Patangay | A61B 5/0295 600/528 |
| 2004/0167417 A1 | 8/2004 | Schulhauser et al. | |
| 2007/0043299 A1 | 2/2007 | Wariar et al. | |
| 2012/0041317 A1* | 2/2012 | Patangay | A61B 7/00 600/483 |
| 2014/0378851 A1* | 12/2014 | Frei | A61B 5/0245 600/508 |
| 2015/0065814 A1* | 3/2015 | Kapoor | A61B 5/0022 600/301 |
| 2018/0008206 A1 | 1/2018 | Stahmann et al. | |
| 2018/0020930 A1 | 1/2018 | An et al. | |

OTHER PUBLICATIONS

"International Application Serial No. PCT/US2019/016846, International Search Report dated May 15, 2019", 5 pgs.

"International Application Serial No. PCT/US2019/016846, Written Opinion dated May 15, 2019", 5 pgs.

Kyoung, Hoon Lim, et al., "Correlation of blood pressure and the ratio of S1 to S2 as measured by esophageal stethoscope and wireless bluetooth transmission", Pakistan Journal of Medical Sciences, vol. 29, No. 4, (Jun. 10, 2016), pp. 1023-1027.

"International Application Serial No. PCT/US2019/016846, International Preliminary Report on Patentability dated Sep. 17, 2020", 8 pgs.

"European Application Serial No. 19707937.9, Response filed Apr. 20, 2021 to Communication pursuant to Rules 161(1) and 162 EPC dated Oct. 15, 2020", 26 pgs.

* cited by examiner

CHRONIC MONITORING OF BLOOD PRESSURE USING HEART SOUNDS

CLAIM OF PRIORITY

This application claims the benefit of priority under 35 U.S.C. § 119(e) of U.S. Provisional Patent Application Ser. No. 62/639,143, filed on Mar. 6, 2018, which is herein incorporated by reference in its entirety.

TECHNICAL FIELD

This document relates generally to medical devices, and more particularly, but not by way of limitation, to systems, devices, and methods for chronic monitoring of blood pressure using heart sounds.

BACKGROUND

Blood pressure is the pressure of circulating blood on the walls of blood vessels, and typically refers to the pressure in large arteries of the systemic system. When further specified, such as left ventricular (UV) pressure, etc., such pressure refers to the pressure in that physiologic component. Blood pressure is commonly expressed in terms of systolic and diastolic pressure. Systolic pressure refers to the maximum pressure during a heart contraction, and diastolic pressure refers to the minimum pressure between to heart contractions, each measured in millimeters of mercury (mmHg).

High blood pressure is a risk factor for mortality, as well as other adverse medical events, including, for example, congestive heart failure, ischemia, arrhythmia, stroke, acute cardiac decompensation, organ failure, etc. High blood pressure is also asymptomatic, so patients don't appreciate their condition until an adverse medical event occurs. Accordingly, it is important to monitor blood pressure information, such as to monitor or assess patient condition or status, including worsening or recovery of one or more physiologic conditions, or to supplement other detections or determinations.

SUMMARY

This document discusses, among other things, systems and methods to determine an indication of contractility of a heart of a patient using received physiologic information, and to determine blood pressure information of the patient using the heart sound information and the determined indication of contractility of the heart. The system can include an assessment circuit configured to determine an indication of contractility of a heart of the patient using first heart sound (S1) information of the patient, and to determine blood pressure information of the patient using second heart sound (S2) information of the patient and the determined indication of contractility of the heart.

An example (e.g., "Example 1") of subject matter (e.g., a system) may include a signal receiver circuit configured to receive physiologic information of a patient, including heart sound information of the patient; and an assessment circuit configured to: determine an indication of contractility of a heart of the patient using the received physiologic information; and determine blood pressure information of the patient using the heart sound information and the determined indication of contractility of the heart.

In Example 2, the subject matter of Example 1 may optionally be configured such that the assessment circuit is configured to determine blood pressure information of the patient using second heart sound (S2) information of the patient.

In Example 3, the subject matter of any one or more of Examples 1-2 may optionally be configured such that the assessment circuit is configured to determine the indication of contractility of the heart using the heart sound information of the patient.

In Example 4, the subject matter of any one or more of Examples 1-3 may optionally be configured such that the assessment circuit is configured to determine the indication of contractility of the heart using first heart sound (S1) information of the patient.

In Example 5, the subject matter of any one or more of Examples 1-4 may optionally be configured such that the assessment circuit is configured to determine blood pressure information of the patient using second heart sound (S2) information of the patient at a specified range of contractility determined using the first heart sound (S1) information of the patient.

In Example 6, the subject matter of any one or more of Examples 1-5 may optionally be configured such that the assessment circuit is configured to:

determine the indication of contractility of the heart for a first cardiac cycle; and if the determined indication of contractility of the heart for the first cardiac cycle is within a threshold range, determine blood pressure information of the patient using the heart sound information for the first cardiac cycle.

In Example 7, the subject matter of any one or more of Examples 1-6 may optionally be configured such that the assessment circuit is configured to: determine the indication of contractility of the heart for the first cardiac cycle using first heart sound (S1) information from the first cardiac cycle of the patient; and if the determined indication of contractility of the heart for the first cardiac cycle is within the threshold range, determine blood pressure information of the patient using second heart sound (S2) information from the first cardiac cycle of the patient.

In Example 8, the subject matter of any one or more of Examples 1-7 may optionally be configured such that the threshold range has an upper boundary threshold amount above a median S1 value for the patient. In an example, the upper boundary of the threshold range can be 25% greater than the median S1 value for the patient. In other examples, the threshold range can be one or more other values.

In Example 9, the subject matter of any one or more of Examples 1-8 may optionally be configured to include a heart sound sensor configured to detect heart sound information from the patient and to determine first heart sound (S1) information and second heart sound (S2) information using the heart sound information, wherein the signal receiver circuit is configured to receive physiologic information of the patient including the first heart sound (S1) information and the second heart sound (S2) information.

In Example 10, the subject matter of any one or more of Examples 1-9 may optionally be configured such that the first heart sound (S1) information includes at least one of a first heart sound (S1) amplitude or energy, and the second heart sound (S2) information includes at least one of a second heart sound (S2) amplitude or energy.

An example (e.g., "Example 11") of subject matter at least one machine-readable medium) may include instructions that, when performed by a medical device, cause the medical device to: receive physiologic information of a patient, including heart sound information of the patient; determine an indication of contractility of a heart of the patient using the received physiologic information; and determine blood pressure information of the patient using the heart sound information and the determined indication of contractility of the heart.

In Example 12, the subject matter of Example 11 may optionally be configured such that the instructions that, when performed by the medical device, cause the medical device instructions to determine the indication of contractility of the heart include instructions to determine the indication of contractility of the heart using first heart sound (S1) information of the patient.

In Example 13, the subject matter of any one or more of Examples 11-12 may optionally be configured such that the instructions that, when performed by the medical device, cause the medical device to determine blood pressure information of the patient using the heart sound information include instructions to determine blood pressure information of the patient using second heart sound (S2) information of the patient.

In Example 14, the subject matter of any one or more of Examples 11-13 may optionally be configured such that the instructions that, when performed by the medical device, cause the medical device to determine blood pressure information of the patient using second heart sound (S2) information include instructions to determine blood pressure information of the patient using second heart sound (S2) information of the patient at a specified range of contractility determined using the first heart sound (S1) information of the patient.

An example (e.g., "Example 15") of subject matter (e.g., a method) may include receiving physiologic information of a patient, including heart sound information of the patient, using a signal receiver circuit; determining, using an assessment circuit, an indication of contractility of a heart of the patient using the received physiologic information; and determining, using the assessment circuit, blood pressure information of the patient using the heart sound information and the determined indication of contractility of the heart.

In Example 16, the subject matter of Example 15 may optionally be configured such that determining the indication of contractility of the heart includes using first heart sound (S1) information of the patient, wherein determining the blood pressure information of the patient includes using second heart sound (S2) information of the patient.

In Example 17, the subject matter of any one or more of Examples 15-16 may optionally be configured such that determining the blood pressure information of the patient includes using the second heart, sound (S2) information of the patient at a specified range of contractility determined using the first heart sound (S1) information of the patient.

In Example 18, the subject matter of any one or more of Examples 15-17 may optionally be configured such that the first heart sound (S1) information of the patient includes at least one of a first heart sound (S1) amplitude or energy, and the second heart sound (S2) information of the patient includes at least one of a second heart sound (S2) amplitude or energy.

In Example 19, the subject matter of any one or more of Examples 15-18 may optionally be configured such that determining the indication of contractility of the heart includes determining the indication of contractility of the heart for the first cardiac cycle using first heart sound (S1) information from the first cardiac cycle of the patient, wherein, if the determined indication of contractility of the heart for the first cardiac cycle is within the threshold range, determining blood pressure information of the patient includes using second heart sound (S2) information from the first cardiac cycle of the patient.

In Example 20, the subject matter of any one or more of Examples 15-19 may optionally be configured such that the threshold range has an upper boundary threshold amount above a median S1 value for the patient.

An example (e.g., "Example 21") of subject matter (e.g., a system or apparatus) may optionally combine any portion or combination of any portion of any one or more of Examples 1-20 to include "means for" performing any portion of any one or more of the functions or methods of Examples 1-20, or a "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
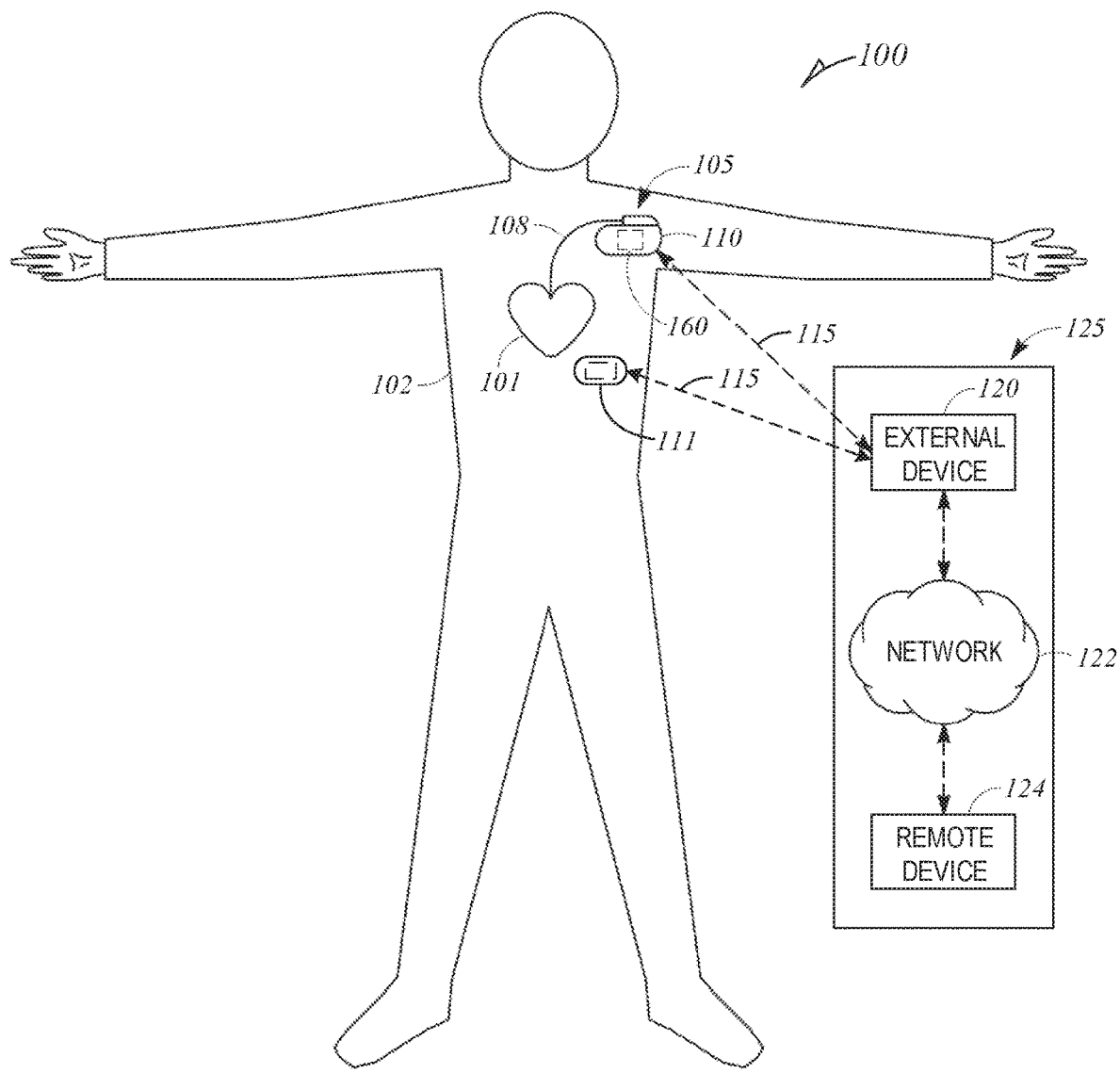
FIG. 1 illustrates an example patient management system and portions of an environment in which the system may operate.

Traditional blood pressure measurements include those taken non-invasively, such as using a mercury manometer, or a blood pressure cuff. However, such measurements can be burdensome, are often inaccurate, discontinuous (e.g., hourly or daily intervals, etc.), and when used for ambulatory or chronic measurements, often suffer from lack of patient compliance. In contrast, implanted systems including a blood pressure sensor that continuously measures blood pressure can be unnecessarily invasive or require additional, otherwise unnecessary sensors, increasing system complexity and cost. An implanted pressure sensor is not appropriate for out-patient or long-term use. Moreover, implanted systems that continuously determine or infer blood pressure (e.g., at intervals more frequent than hourly or daily, such as at each cardiac cycle, or periods of cardiac cycles, etc.) using one or more other sensors can be inaccurate, in certain examples, including periods of noise or inaccurate measurement, or require frequent and costly calibration to maintain accuracy. It can be beneficial to more accurately determine blood pressure, in certain examples, reducing such periods of noise or inaccurate measurement, and moreover, to determine blood pressure using existing, dual-purpose, or multi-use sensors, in certain examples, different from a dedicated pressure sensor, reducing cost or complexity of ambulatory systems. Further, it can be beneficial to continuously determine blood pressure, at each cardiac cycle, or at each qualifying cardiac cycle.

Heart sounds are recurring mechanical signals associated with cardiac vibrations from blood flow through the heart with each cardiac cycle, and can be separated and classified according to activity associated with the vibrations and blood flow. Heart sounds include four major sounds: the first through the fourth heart sounds. The first heart sound (S1) is the vibrational sound made by the heart during closure of the atrioventricular (AV) valves, the mitral valve and the tricuspid valve, at the beginning of systole. The second heart sound (S2) is the vibrational sound made by the heart during closure of the aortic and pulmonary valves at the beginning of diastole. The third and fourth heart sounds (S3, S4) are related to filling pressures of the left ventricle during diastole.

Filling of the left ventricle from the left atrium begins as the left ventricle relaxes following a contraction, and the pressure in the left ventricle falls below the pressure of the left atrium, opening the mitral valve. As the left ventricle contracts, the pressure in the left ventricle quickly rises. When the pressure in the left ventricle rises above the pressure of the left atrium, the mitral valve snaps shut, isolating the left ventricle from the left atrium, resulting in the first heart sound. Close in time to the closure of the mitral valve, when the pressure in the left ventricle rises above the pressure of the aorta, the aortic valve opens, allowing blood to exit the left ventricle for the rest of the body through the aorta. The maximum pressure in the left ventricle during contraction, the systolic pressure, is representative of the maximum systemic pressure in the arteries following contraction of the left ventricle (e.g., typically 100-140 mmHg, etc.).

As the left ventricle relaxes, the pressure in the left ventricle drops. When the pressure in the left ventricle falls below the pressure of the aorta, the aortic valve snaps shut, isolating the left ventricle from the aorta, resulting in the second heart sound. The pressure in the arterial system at the time of the aortic valve opening is the systemic diastolic pressure (e.g., typically 60-100 mmHg, etc.). Close in time to the closure of the aortic valve, when the pressure in the left ventricle falls below the pressure of the left atrium, the mitral valve opens, filling the left ventricle. The minimum pressure in the left ventricle following contraction is the left ventricular diastolic pressure (e.g., typically down to 5-10 mmHg, etc.), different in amplitude, and possibly time, than the systemic diastolic pressure.

The heart valves change states between open and closed at various times during the cardiac cycle. These valve state changes occur when specific relative pressures are present within the heart and the major vessels leading from the heart (e.g., the aorta). Both the valve state changes and the effects of the state changes are detectable through various methods. For example, valve closure cause vibrations of the walls of the heart that can be detected using an accelerometer or a microphone. The movement of the valves can be detected directly via imaging technologies such as echocardiography and magnetic resonance imaging (MRI) or by intracardiac impedance plethysmography.

Various physiologic conditions can be detected using heart sounds, including, for example, acute physiologic events, such as one or more abnormal cardiac rhythms (e.g., atrial fibrillation, atrial flutter, cardiac mechanical dyssynchrony, etc.), as well as more chronic physiologic events, such as congestive heart failure, ischemic, etc.

Further, heart sounds can be correlated with certain physiologic information, such that, in certain examples, heart sound information can be used as a surrogate for, or to detect one or more physiologic characteristics. For example, heart sounds can be used to detect atrial filling pressure, such as illustrated in the commonly assigned Siejko et al. U.S. Pat. No. 7,972,275, titled "Method and Apparatus for Monitoring of Diastolic Hemodynamics", or the commonly assigned Patangay et al. U.S. Pat. No. 8,048,001, titled "Method and Apparatus for Detecting Atrial Filling Pressure", each of which are hereby incorporated by reference in their entirety.

Heart sounds are generally related to blood pressure. Chronic monitoring of blood pressure based on the frequency and/or amplitude components of first and second heart sounds have been proposed. However, the present inventors have recognized, among other things, that the relationship between heart sounds and blood pressure changes according to different, interdependent variables, that in certain examples, heart sounds track blood pressure, but other times it does not, and that, accordingly, certain ventricular functions or physiologic information can be used to identify periods of increased and decreased correlation between blood pressure and heart sounds. The increase and decrease in correlation can be used to increase the sensitivity or specificity of blood pressure detection using heart sounds, or to increase the efficiency of data collection and storage to accurately monitor blood pressure using heart sounds. Accordingly, the methods and systems described herein can provide a for more robust blood pressure monitoring, in certain examples, using less storage or data processing than existing ambulatory systems or devices.

Ambulatory medical devices, including implantable, leadless, or wearable medical devices, can be configured to monitor, detect, or treat various cardiac conditions. Various ambulatory medical devices can be implanted in a patient's body or otherwise positioned on or about the patient to monitor patient physiologic information, such as heart sounds, respiration (e.g., respiration rate, tidal volume, etc.), impedance (e.g., thoracic impedance, cardiac impedance, etc.), pressure (e.g., blood pressure), cardiac activity (e.g., heart rate), physical activity, posture, or one or more other physiologic parameters of a patient, or to provide electrical stimulation or one or more other therapies or treatments to optimize or control contractions of the heart.

Traditional cardiac rhythm management (CRM) devices, such as pacemakers, defibrillators, or cardiac monitors, include subcutaneous devices configured to be implanted in a chest of a patient, having one or more leads to position one or more electrodes or other sensors at various locations in the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient.

Leadless cardiac pacemakers (LCP) include small (e.g., smaller than traditional implantable CRM devices), self-contained devices configured to detect physiologic information from or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the patient without required implant or an in-patient procedure for placement, battery replacement, or repair. However, such sensors and devices, in contrast to implantable, subcutaneous, or leadless medical devices, may have reduced patient compliance, increased detection noise, or reduced detection sensitivity.

For each ambulatory device described above (e.g., implantable, leadless, or wearable medical devices, etc.), each additional sensor can increase system cost and complexity, reduce system reliability, or increase the power consumption and reduce the usable life of the ambulatory device. Accordingly, it can be beneficial to use a single sensor to determine multiple types of physiologic information. In an example, an accelerometer, acoustic sensor, or other heart sound sensor can be used to determine heart sound information of the patient, as well as blood pressure information or one or more other types of physiologic information of the patient. An assessment circuit can determine blood pressure information of the patient using heart sound information, and in certain examples, determine a patient status or risk or stratification of worsening patient condition using the determined blood pressure information, and provide an alert or indication to the patient or a clinician that the patient seek medical treatment or be hospitalized in response to such determination.

FIG. 1 illustrates an example patient management system 100 and portions of an environment in which the system 100 may operate. The patient management system 100 can perform a range of activities, including remote patient monitoring and diagnosis of a disease condition. Such activities can be performed proximal to a patient 102, such as in a patient home or office, through a centralized server, such as in a hospital, clinic, or physician office, or through a remote workstation, such as a secure wireless mobile computing device.

The patient management system 100 can include an ambulatory system 105, an external system 125, and a communication link 115 providing for communication between the ambulatory system 105 and the external system 125.

The ambulatory system 105 can include an implantable medical device (IMD) 110, one or more leadless cardiac pacemakers (LCP), a wearable medical device 111, or one or more other implantable, leadless, subcutaneous, external, or wearable medical device configured to monitor, sense, or detect information from, determine physiologic information about, or provide one or more therapies to treat various cardiac conditions of the patient 102, such as an ability of a heart to sufficiently deliver blood to a body, including atrial fibrillation (AF), congestive heart failure (CHF), hypertension, or one or more other cardiac conditions.

In an example, the IMD 110 can include one or more traditional cardiac rhythm management (CRM) devices, such as a pacemaker, defibrillator, or cardiac monitor, implanted in a chest of a patient, having a lead system 108 including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 102.

The IMD 110 can include an assessment circuit 160 configured to detect or determine specific physiologic information of the patient 102, or to determine one or more conditions or provide information or an alert to a user, such as the patient 102, a clinician, or one or more other caregivers. The IMD 110 can alternatively or additionally be configured as a therapeutic device configured to treat one or more medical conditions of the patient 102. The therapy can be delivered to the patient 102 via the lead system 108 and associated electrodes, or using one or more other delivery mechanisms. The therapy can include anti-arrhythmic therapy to treat an arrhythmia or to treat or control one or more complications from arrhythmias, such as syncope, congestive heart failure (CHF), or stroke, among others. Examples of the anti-arrhythmic therapy include pacing, cardioversion, defibrillation, neuromodulation, drug therapies, or biological therapies, among other types of therapies. In other examples, therapies can include cardiac resynchronization therapy (CRT) for rectifying dyssynchrony and improving cardiac function in CHF patients. In some examples, the IMD 110 can include a drug delivery system, such as a drug infusion pump to deliver drugs to the patient for managing arrhythmias or complications from arrhythmias, hypertension, or one or more other physiologic conditions. In yet other examples, the IMD 100 can include a therapy circuit or module configured to treat hypertension (e.g., a neuro-stimulation therapy circuit, a drug delivery therapy circuit, a stimulation therapy circuit, etc.).

The wearable medical device 111 can include one or more wearable or external medical sensors or devices (e.g., automatic external defibrillators (AEDs), Holter monitors, patch-based devices, smart watches, smart accessories, wrist- or finger-worn medical devices, etc.). The wearable medical device 111 can include an optical sensor configured to detect a photoplethysmogram (PPG) signal on a wrist, finger, or other location on the patient. In other examples, the wearable medical device 111 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 100 can include, among other things, a respiration sensor configured to receive respiration information e.g., a respiration rate (RR), a respiration volume (tidal volume), etc.), a heart sound sensor configured to receive heart sound information, a thoracic impedance sensor configured to receive impedance information, a cardiac sensor configured to receive cardiac electrical information, and an activity sensor configured to receive information about a physical motion (e.g., activity, posture, etc.), or one or more other sensors configured to receive physiologic information of the patient 102.

The external system 125 can include a dedicated hardware/software system, such as a programmer, a remote server-based patient management system, or alternatively a system defined predominantly by software running on a standard personal computer. The external system 125 can manage the patient 102 through the IMD 110 connected to the external system 125 via a communication link 115. In other examples, the IMD 110 can be connected to the wearable device 111, or the wearable device 111 can be connected to the external system 125, via the communication link 115. This can include, for example, programming the IMD 110 to perform one or more of acquiring physiological data, performing at least one self-diagnostic test (such as for a device operational status), analyzing the physiological data to detect a cardiac arrhythmia, or optionally delivering or adjusting a therapy to the patient 102. Additionally, the external system 125 can send information to, or receive information from, the IMD 110 or the wearable device 111 via the communication link 115. Examples of the information can include real-time or stored physiological data from the patient 102, diagnostic data, such as detection of cardiac arrhythmias or events of worsening heart failure, responses to therapies delivered to the patient 102, or device operational status of the IMD 110 or the wearable device 111 (e.g., battery status, lead impedance, etc.). The communication link 115 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 125 can include an external device 120 in proximity of the IMD 110, and a remote device 124 in a location relatively distant from the IMD 110 in communication with the external device 120 via a telecommunication network 122. Examples of the external device 120 can include a medical device programmer.

The remote device 124 can be configured to evaluate collected patient information and provide alert notifications, among other possible functions. In an example, the remote device 124 can include a centralized server acting as a central hub for collected patient data storage and analysis. The server can be configured as a uni-, multi-, or distributed computing and processing system. The remote device 124 can receive patient data from multiple patients including, for example, the patient 102. The patient data can be collected by the IMD 110, among other data acquisition sensors or devices associated with the patient 102. The server can include a memory device to store the patient data in a patient database. The server can include an alert analyzer circuit to evaluate the collected patient data to determine if specific alert condition is satisfied. Satisfaction of the alert condition may trigger a generation of alert notifications. In some examples, the alert conditions may alternatively or additionally be evaluated by the IMD 110. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 124 may additionally include one or more locally configured clients or remote clients securely connected over the network 122 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 124, including the server and the interconnected clients, may also execute a follow-up scheme by sending follow-up requests to the IMD 110, or by sending a message or other communication to the patient 102, clinician or authorized third party as a compliance notification.

The network 122 can provide wired or wireless interconnectivity. In an example, the network 122 can be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 120 or the remote device 124 can include a respective display unit for displaying the physiological or functional signals, or alerts, alarms, emergency calls, or other forms of warnings to signal the detection of arrhythmias. In some examples, the external system 125 can include an external data processor configured to analyze the physiological or functional signals received by the IMD 110, and to confirm or reject the detection of arrhythmias. Computationally intensive algorithms, such as machine-learning algorithms, can be implemented in the external data processor to process the data retrospectively to detect cardia arrhythmias.

Portions of the IMD 110 or the external system 125 can be implemented using hardware, software, firmware, or combinations thereof. Portions of the 110 or the external system 125 can be implemented using an application-specific circuit that can be constructed or configured to perform one or more functions, or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

Figure 2A:
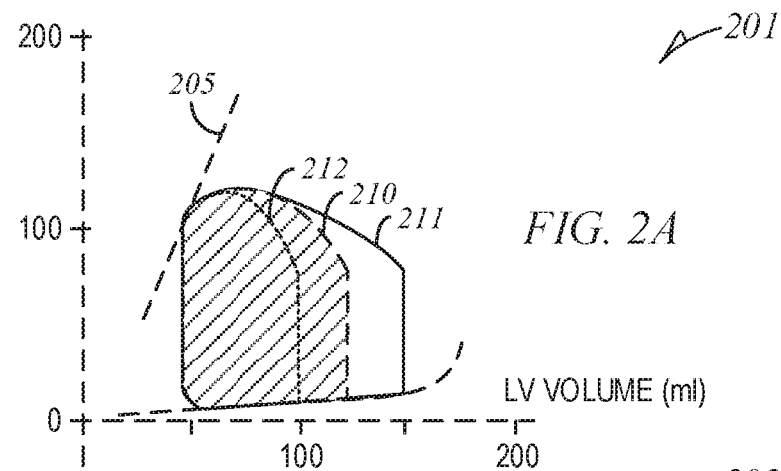
FIGS. 2A-2C illustrate example relationships between left ventricular (LV) pressure and LV volume with different levels of preload, afterload, and inotropy.
Figure 2B:
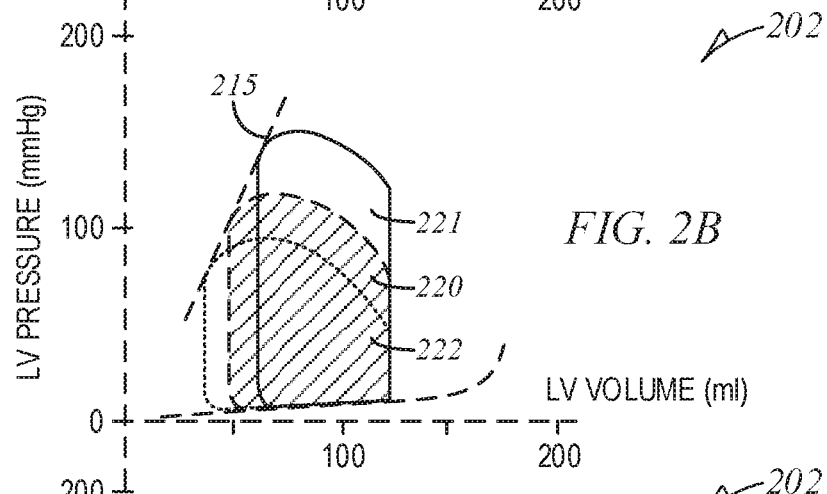
Figure 2C:
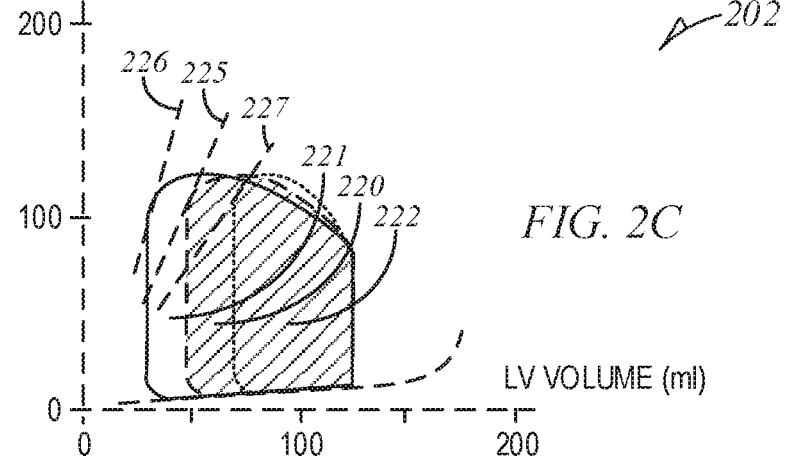

FIGS. 2A-2C illustrate example pressure-volume (PV) loops showing relationships between left ventricular (LV)

pressure and LV volume at different levels of preload, afterload, and inotropy, each interdependent variables that affect ventricular function.

Preload refers to the initial stretch of the cardiac myocytes prior to contraction, and is therefore related to muscle sarcomere length. As blood volume increases, end-diastolic pressure and volume of the ventricles increase, which stretches the sarcomeres, increasing preload. In contrast, as blood volume decreases, ventricular filling decreases, which shortens sarcomere lengths, decreasing preload.

Afterload refers to the load the heart must eject blood against, and is closely related to aortic pressure, unless aortic stenosis is present. Afterload is often expressed as ventricular wall stress ($\sigma$):

$$\sigma \propto \frac{P \times r}{h} \tag{1}$$

where P is ventricular pressure, r is ventricular radius, and h is wall thickness.

Inotropy, or contractility, refers to the force or energy of muscle contraction, or fiber shortening. As inatropy increases, active tension increases for a given preload, which increases the rate of pressure change (e.g., dP/dt) during isovolumetric contraction.

At the bottom left corner of the PV loop, the mitral valve opens. The LV volume increases during diastole until the bottom right corner of the PV loop, at the end of diastole, where the mitral valve closes, and systole begins. LV pressure increases during isovolumetric contraction until the upper right corner of the PV loop, where the aortic valve opens. LV volume decreases through ejection until the upper left corner of the PV loop, at the end of systole, where the aortic valve closes, and diastole begins. LV pressure decreases during isovolumetric relaxation until the mitral valve opens. The width of the PV loop (end-diastolic volume minus end-systolic volume) is stroke volume (SV).

FIG. 2A illustrates a first pressure-volume (PV) loop 201 showing a relationship between left ventricular (LV) pressure and LV volume at different levels of preload (e.g., Control 210, Increased Preload 211, and Decreased Preload 212). As preload increases, stroke volume increases. Likewise, as preload decreases, stroke volume decreases. However, preload does not significantly affect LV end-systolic pressure (LVESP). The width of the PV loop changes with preload, not the height. Moreover, preload does not affect the end-systolic pressure-volume relationship (ESPVR) 205.

FIG. 2B illustrates a second PV loop 202 showing a relationship between LV pressure and LV volume at different levels of afterload (e.g., Control 220, Increased Afterload 221, and Decreased Afterload 222). As afterload increases, stroke volume decreases, and LV end-systolic pressure and volume increase. Likewise, as afterload decreases, stroke volume increases, and LV end-systolic pressure and volume decrease. However, changes in afterload do not significantly affect LV end-diastolic volume, or ESPVR 215.

FIG. 2C illustrates a PV loop showing a relationship between LV pressure and LV volume at different levels of inotropy (e.g., Control 220, increased Afterload 221, and Decreased Afterload 222). As inotropy increases, stroke volume increases, and LV end-systolic volume decreases. As inotropy decreases, stroke volume decreases, and LV end-systolic volume increases. Accordingly, changes in inotropy affect the end-systolic pressure-volume relationship (ES-PVR) 225-227, illustrated as the sloped, dashed lines in FIG. 2C, one for each level of inotropy. However, changes in inotropy do not significantly affect end-systolic pressure, or LV end-diastolic volume.

FIGS. 2A-2C illustrate that changes in preload or inotropy do not significantly affect LV end-systolic pressure, that changes in afterload or inotropy do not significantly affect LV end-diastolic volume, and that changes in preload or afterload do not significantly affect the end-systolic pressure-volume relationship (ESPVR), whereas changes in inotropy do affect ESPVR.

To study the effect of afterload and contractility changes on heart sounds and blood pressure, phenylepherine and nitroglycerine were used to change afterload, and dobutamine was used to change contractility. The present inventors recognized, among other things, that whereas the relationship between S2 and blood pressure changes substantially holds with changes in afterload, the relationship between S2 and blood pressure is significantly affected by changes in contractility. Further, the present inventors have recognized that constant contractility states, or states without significant contractility changes, can be identified using S1, as S1 is substantially correlated to contractility. Thus, changes in contractility, and accordingly S1, can identify periods of time where S2 substantially tracks blood pressure, and times when it does not. Accordingly, S1 can be used to exclude segments with substantial contractility changes that adversely impact S2 correlation to blood pressure, and thus, the ability of S2 to track blood pressure. Alternatively, S1 can be used to adjust the S2 measurement to maintain its correlation to blood pressure.

In an example, S1 values outside a median S1 value can be used to detect periods of substantial contractility change. S1 values at or near a median value can be used to identify periods without substantial contractility change (e.g., within 25% of a median S1 value). In other examples, S1 values outside a threshold (e.g., S1 values greater than 25% above a median S1 value) can be used to identify periods of substantial contractility change, and thus, periods of decreased S2 correlation to blood pressure.

In other examples, S2 at a fixed value or range of values of S1 can be used as a marker of blood pressure. In an example, S2 can be recorded and used for blood pressure calculation only if the corresponding S1 is within a range of acceptable S1 values. In other examples, S2 can be recorded or logged at different levels of S1, where changing S1 values can indicate different levels of inotropy, such as to monitor blood pressure as a function of inotropic state (e.g., exercise, etc.). In other examples, S2 can be recorded or monitored at specific levels or ranges of S1, heart rate, impedance, systolic time intervals, or specific combinations thereof (e.g., S1 and heart rate, etc.).

In an example, average daily values, or average values of other shorter or longer time periods (e.g., wake hours, sleeping hours, periods of activity or inactivity during a day, long-term (e.g., 30-day, 60-day, etc.) average, etc.) can be determined at a given S1 value or range of S1 values, or at one or more other indications of contractility. For example, sleeping blood pressure can be used to determine systemic drift. In other examples, in addition to, or instead of, using S1, S2 can be corrected using, for example, systolic time intervals (STIs), pre-ejection period (PEP), Q-S2 time period, left ventricular ejection time (LVET), LV dP/dt, etc.

In an example, an indication of contractility can be correlated to activity, and thus, certain ranges of contractility can be used to determine a resting blood pressure, a blood pressure at light activity (e.g., normal function), or a blood pressure at high activity (e.g., exercise, etc.). In other examples, contractility can be correlated to activity, posture, or combinations thereof, for example, using an accelerometer, a posture sensor (e.g., a magnetometer), or other activity sensor (e.g., step count, rate of steps, etc.). Ranges can correspond to different levels of activity, posture, etc., or other sensors (e.g., heart rate, activity, etc.) can be used to further log blood pressure at different levels of physiological information (e.g., contractility, activity, heart rate, respiration, etc.). Different tables can be created corresponding to different conditions or information. For example, tables of S2 can be created at a given S1 or range of S1, alone or in combination with a given value or range of values of one or more other condition or information, including, for example, heart rate, activity, posture, respiration (e.g., rate, pattern, mode, etc.), etc. In other examples, S2 or blood pressure measurements or determinations can be triggered using different physiologic information (e.g., activity, etc.).

In other examples, blood pressure information can further be determined using S2 information in combination with one or more other physiologic information, such as a determination or indication of one or more other conditions, etc. For example, if a patient has valvular heart disease, the determination of blood pressure can be adapted to account for such condition, either detected using physiologic information or received from an ambulatory or external system (e.g., medical records, input from a physician, etc.). Mitral valve defects can affect S1, whereas aortic valve defects can affect S2. The ambulatory or external system can detect (e.g., using heart sound morphology, etc.) or receive indications of such conditions, and can adapt the determination of blood pressure accordingly. In other examples, split S1 or S2 can be accounted for using, for example, only the largest peak, an average of two peaks, the first peak, etc.

In an example, S1 may have a higher spectral content (e.g., energy shifted to higher frequencies) with contractility increases. Accordingly, spectral content of heart sounds can be used to determine an indication of contractility. In an example, a filter can be used to filter frequencies associated with normal, low-contractility states. The output of that filter can be monitored, and when the unfiltered content (e.g., an aggregate, integral, RMS, or amplitude) exceeds a threshold, S2 can be disregarded for determinations of blood pressure, or the determinations of blood pressure can be marked as being determined in a high-contractility state. Moreover, the morphology of S1 changes with contractility. In an example, the width (e.g., time) of the S1 can decrease, or the slope of the S1 can increase, with increases in contractility. Accordingly, S2 can be disregarded or logged using different S1 morphology characteristics corresponding to various indications of contractility. In other examples, the spectral content of the S2 (e.g., an increase in higher frequencies can indicate a higher blood pressure), or the ratio of S2 to S1 can be used to further determine S2 correlation to blood pressure.

Figure 3:
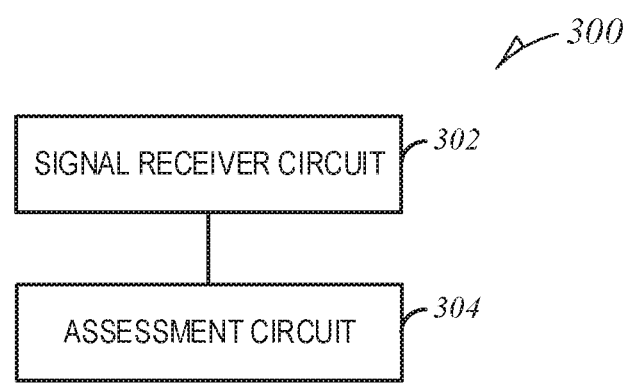
FIG. 3 illustrates an example system including a signal receiver circuit and an assessment circuit.

FIG. 3 illustrates an example system 300 including a signal receiver circuit 302 and an assessment circuit 304. In an example, one or both of the signal receiver circuit 302 or the assessment circuit 304 can be included in the ambulatory system 105 or the external system 125. In other examples, one of the signal receiver circuit 302 or the assessment circuit 304 can be included in the ambulatory system 105, and the other in the external system 125. In other examples, the ambulatory system 105 and the external system 125 can include aspects of each of the signal receiver circuit 302 and the assessment circuit 304.

The signal receiver circuit 302 can be configured to receive physiologic information of a patient, including, for example, heart sound information of a heart of a patient (e.g., first, second, third, or fourth heart sounds (S1-S4), etc.), or one or more other physiologic information from the patient, such as contractility information, impedance information, respiration information, cardiac electrical information, or one or more other type of physiologic information from the patient. In an example, the physiologic information can include one or more of a heart rate (e.g., chronotropy), posture, activity, one or more cardiac electrical or mechanical intervals (e.g., systolic time intervals (STIs), such as a pre-ejection period (PEP), Q-S2 time period, left ventricular ejection time (LVET), LV dP/dt, etc.), a time interval between cardiac electrical events, cardiac mechanical events, or a cardiac electrical event and a cardiac mechanical event, etc.

In an example, the system 300 can include a heart sound sensor, such as an accelerometer, a microphone, or other mechanical or acoustic sensor configured to sense heart sound information from a heart of a patient. The heart sound sensor can be a component in the ambulatory system 105. In other examples, the ambulatory system 105 or the external system 125 can be configured to receive heart sound information, such as from the heart of the patient.

The assessment circuit 304 can be configured to determine an indication of contractility of a heart of the patient using the received physiologic information. In an example, contractility of the heart can be determined using S1 information of the patient, or one or more other heart sound measurement, timing, or value. For example, changes in contractility are reflected in S1 amplitude information, energy information (e.g., integrated energy or amplitude, RMS energy, spectral content, etc.). In certain examples, S1 information can be used to determine an indication of contractility. In other examples, contractility can be determined using systolic time intervals, one or more other cardiac electrical or mechanical intervals, impedance plethysmography, or other impedance variations of the patient.

The assessment circuit 304 can be configured to determine blood pressure information of the patient using heart sound information. In an example, S2 information can be used to determine blood pressure information. The relationship between S2 and blood pressure is affected by contractility. Accordingly, the assessment circuit 304 can be configured to determine blood pressure information using heart sound information (e.g., S2 information) and a determined indication of contractility of the heart (e.g., determined using S1 information).

For example, the assessment circuit 304 can determine a specified range of contractility using S1 information, or use a specified range of S1 information to determine an indication of contractility (e.g., an S1 value or increase in S1 value greater than a mean or median S1 value or threshold value, such as a 25% increase in a median S1 value, etc.). In an example, if the indication of contractility is below or inside of a specified value or range of values (e.g., S1 value for a cardiac cycle or number of cardiac cycles), the blood pressure information can be determined using heart sound information (e.g., S2 value for the cardiac cycle or the corresponding number of cardiac cycles). In contrast, if the indication of contractility is above or outside of the specified value or range of values (e.g., for a cardiac cycle or number of cardiac cycles), the blood pressure information can be disregarded or not determined (e.g., for the cardiac cycle or the corresponding number of cardiac cycles).

Figure 4:
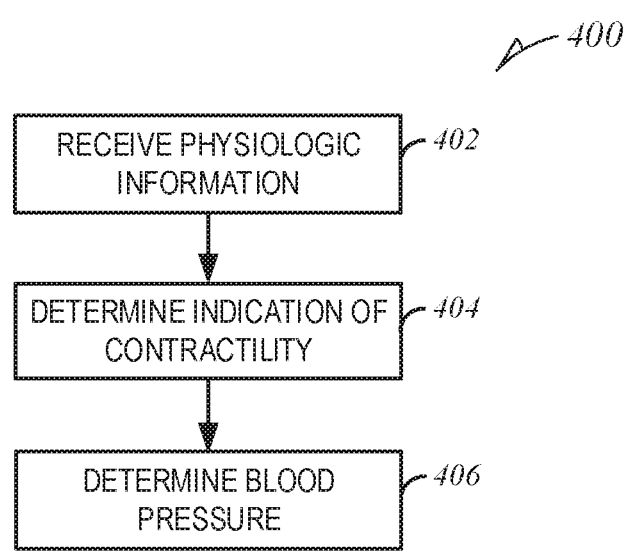
FIGS. 4-5 illustrate example methods to determine blood pressure information using determined indications of contractility.

FIG. 4 illustrates an example method 400 to determine blood pressure information using determined indications of contractility. At 402, physiologic information of a patient can be received, such as using a signal receiver circuit of an ambulatory system or an external system. The physiologic information can include heart sound information, one or more other types of physiologic information (e.g., respiration, heart rate, impedance, cardiac electrical information, etc.), or combinations thereof, such as detected using one or more sensors (e.g., a heart sound sensor, an impedance sensor, an electrode, etc.) of one or more ambulatory devices. The signal receiver circuit can be coupled (e.g., communicatively coupled) to the one or more sensors, or the signal receiver circuit can be configured to receive the physiologic information from one or more external systems coupled to the one or more sensors.

At 404, an indication of contractility of a heart of the patient can be determined using the received physiologic information, such as using an assessment circuit of an ambulatory system or an external system. In an example, the indication of contractility of the heart can be determined using heart sound information, such as S1 information of the patient. In other examples, the indication of contractility can be determined using other received physiologic information, or a combination of received physiologic information (e.g., S1 information and heart rate information, etc.).

At 406, a blood pressure of the patient can be determined using heart sound information (e.g., S2 information) and the determined indication of contractility of the heart (e.g., S1 information). In an example, the blood pressure information can be determined using S2 information at a specified value or range of S1 information. In an example, the specified value or range of S1 information can correspond to a level of contractility of the heart. For example, if the S1 information indicates that the contractility of the heart is high, such as using a value of S1 information above a threshold (e.g., 25% above a mean or median value, etc.). In certain examples, one or more other thresholds can be used corresponding to a determination of contractility of the heart being higher than a median or mean value or a normal range about a median or mean value, either patient-specific or population-based.

Figure 5:
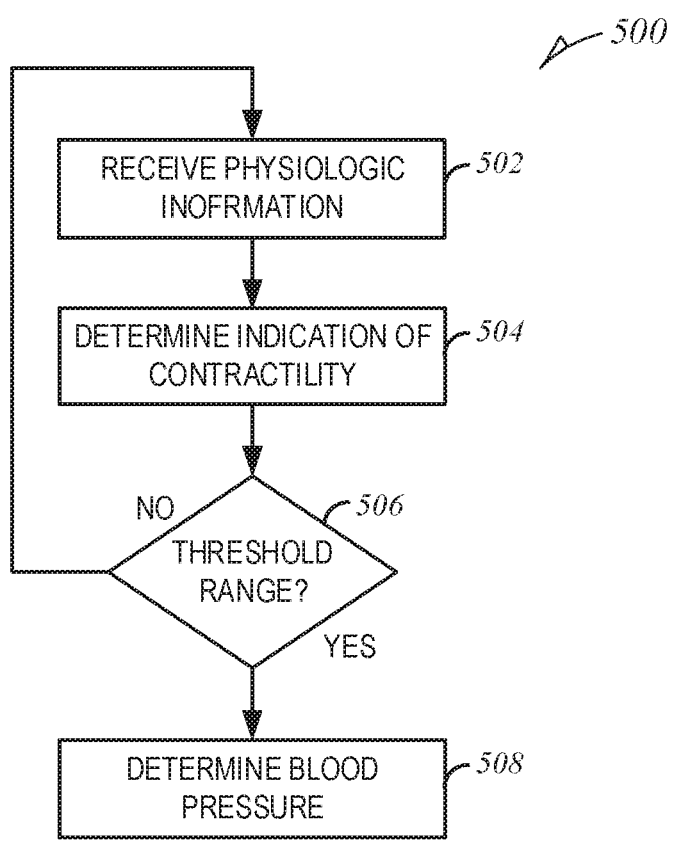

FIG. 5 illustrates an example method 500 to determine blood pressure information using determined indications of contractility. At 502, physiologic information is received. At 504, an indication of contractility is determined using the received physiologic information. At 506, if the determined indication, or received physiologic information indicative of contractility, is within a threshold range, for example, for a specific cardiac cycle or a group of cardiac cycles, then a blood pressure for the specific cardiac cycle of the group of cardiac cycles, is determined at 508. If, at 506, the determined indication of contractility is not within the threshold range, process returns to 502. For example, the determined blood pressure can be used to initiate or adjust vagal nerve stimulation, baroreceptor stimulation, or one or more other blood pressure therapies.

In an example, the blood pressure determined at 508 can be used to determine or adjust a therapy, such as one part of a closed loop system. If the determined blood pressure is within a range or above or below a threshold, a therapy can be continued, initiated, or adjusted, depending on the therapy or treatment. If the determined blood pressure is not within a range or above or below a threshold, a therapy can be discontinued, initiated, or adjusted, depending on the therapy or treatment.

Figure 6:
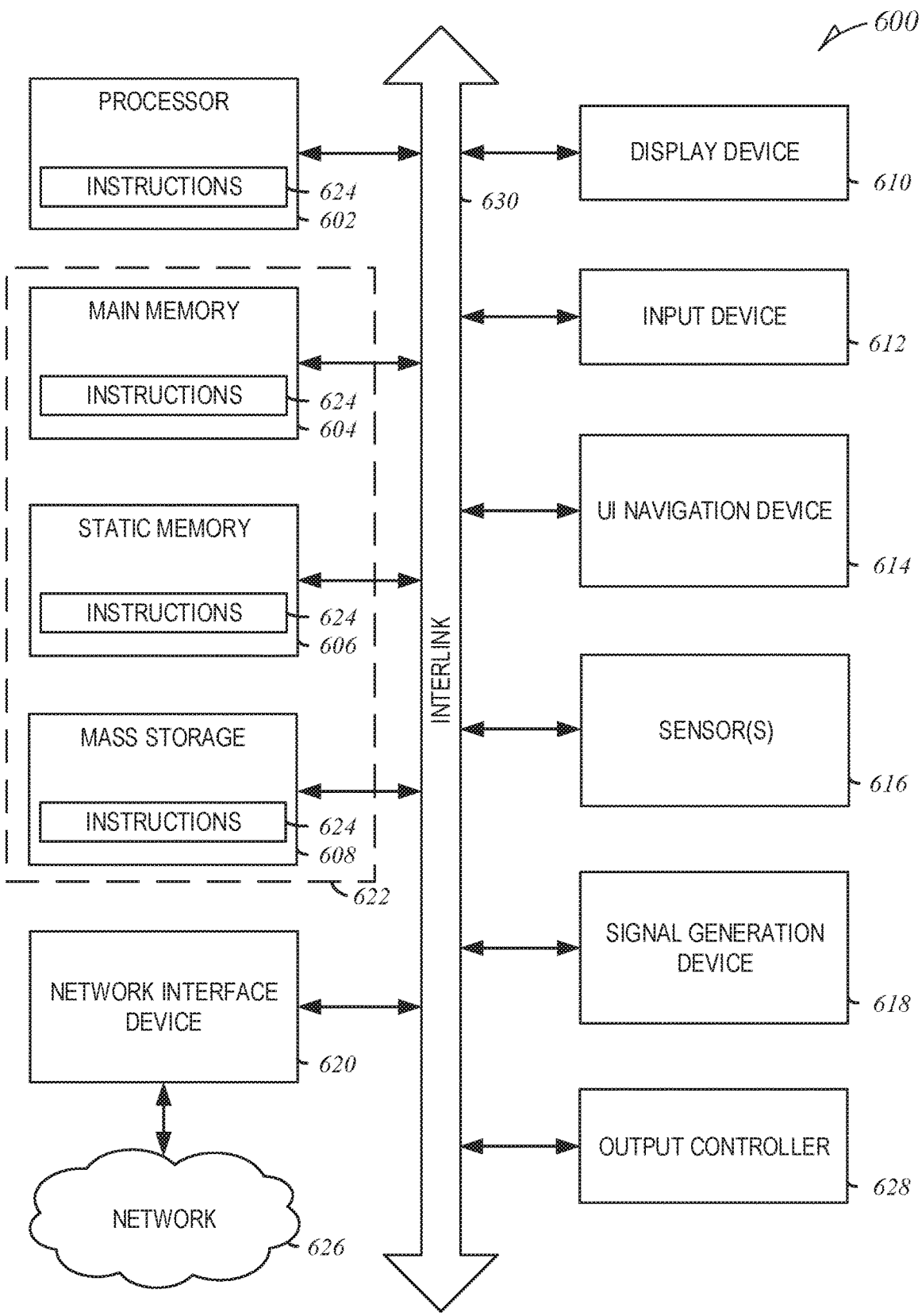
FIG. 6 illustrates a block diagram of an example machine upon which any one or more of the techniques discussed herein may perform.

FIG. 6 illustrates a block diagram of an example machine 600 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 600. Circuitry (e.g., processing circuitry) is a collection of circuits implemented in tangible entities of the machine 600 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, movable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 600 follow.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 600 may include a hardware processor 602 (e.g., a central processing unit (CPU), a graphics processing unit (GPU), a hardware processor core, or any combination thereof), a main memory 604, a static memory (e.g., memory or storage for firmware, microcode, a basic-input-output (BIOS), unified extensible firmware interface (UEFI), etc.) 606, and mass storage 608 (e.g., hard drive, tape drive, flash storage, or other block devices) some or all of which may communicate with each other via an interlink (e.g., bus) 630. The machine 600 may further include a display unit 610, an alphanumeric input device 612 (e.g., a keyboard), and a user interface (UI) navigation device 614 (e.g., a mouse). In an example, the display unit 610, input device 612, and UI navigation device 614 may be a touch screen display. The machine 600 may additionally include a signal generation device 618 (e.g., a speaker), a network interface device 620, and one or more sensors 616, such as a global positioning system (GPS) sensor, compass, accelerometer, or one or more other sensors. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 602, the main memory 604, the static memory 606, or the mass storage 608 may be, or include, a machine-readable medium 622 on which is stored one or more sets of data structures or instructions 624 (e.g., software) embodying or utilized by any one or more of the techniques or functions described herein. The instructions 624 may also reside, completely or at least partially, within any of registers of the processor 602, the main memory 604, the static memory 606, or the mass storage 608 during execution thereof by the machine 600. In an example, one or any combination of the hardware processor 602, the main memory 604, the static memory 606, or the mass storage 608 may constitute the machine-readable medium 622. While the machine-readable medium 622 is illustrated as a single medium, the term "machine-readable medium" may include a single medium or multiple media (e.g., a centralized or distributed database, and/or associated caches and servers) configured to store the one or more instructions 624.

The term "machine-readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may be further transmitted or received over a communications network 626 using a transmission medium via the network interface device 620 utilizing any one of a number of transfer protocols (e.g., frame relay, interact protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
    a signal receiver circuit configured to receive physiologic information of a patient, including heart sound information of the patient; and
    an assessment circuit configured to:
        determine an indication of contractility of a heart of the patient using first heart sound (S1) information from a first cardiac cycle of the patient; and
        if the determined indication of contractility of the heart for the first cardiac cycle is within a threshold range having an upper boundary threshold amount at a median S1 value for the patient, determine blood pressure information of the patient using the heart sound information from the first cardiac cycle.

2. The system of claim 1, wherein, if the determined indication of contractility of the heart for the first cardiac cycle is within the threshold range having the upper boundary threshold amount at the median S1 value for the patient, the assessment circuit is configured to determine systemic arterial blood pressure information of the patient using second heart sound (S2) information from the first cardiac cycle of the patient.

3. The system of claim 1, wherein, if the determined indication of contractility of the heart for the first cardiac cycle is within the threshold range having the upper boundary threshold amount at the median S1 value for the patient, the assessment circuit is configured to determine blood pressure information of the patient using second heart sound (S2) information from the first cardiac cycle of the patient.

4. The system of claim 3, including:
a heart sound sensor configured to detect heart sound information from the patient and to determine the first heart sound (S1) information and the second heart sound (S2) information using the heart sound information,
wherein the signal receiver circuit is configured to receive physiologic information of the patient including the first heart sound (S1) information and the second heart sound (S2) information.

5. The system of claim 4, wherein the first heart sound (S1) information includes at least one of a first heart sound (S1) amplitude or energy, and the second heart sound (S2) information includes at least one of a second heart sound (S2) amplitude or energy.

6. The system of claim 1, wherein, to determine the indication of contractility of the heart of the patient using the first heart sound (S1) information from the first cardiac cycle of the patient, the assessment circuit is configured to determine the indication of contractility of the heart of the patient using at least one of the first heart sound (S1) amplitude or energy from the first cardiac cycle of the patient, and
wherein, to determine blood pressure information of the patient using the heart sound information from the first cardiac cycle, the assessment circuit is configured to determine blood pressure information of the patient using at least one of the second heart sound (S2) amplitude or energy from the first cardiac cycle of the patient.

7. A method, comprising:
receiving physiologic information of a patient, including heart sound information of the patient, using a signal receiver circuit, the heart sound information comprising first heart sound (S1) information of the patient, the first heart sound (S1) information of the patient comprising at least one of a first heart sound (S1) amplitude or energy of the patient;
determining, using an assessment circuit, an indication of contractility of a heart of the patient using at least one of the received first heart sound (S1) amplitude or energy of the patient; and
determining, using the assessment circuit, blood pressure information of the patient using the heart sound information corresponding to a specified range of the determined indication of contractility of the heart, the indication of contractility determined using the at least one of the received first heart sound (S1) amplitude or energy of the patient.

8. The method of claim 7, wherein determining the blood pressure information of the patient includes determining systemic blood pressure information of the patient using second heart sound (S2) information of the patient.

9. The method of claim 8, wherein determining the blood pressure information of the patient includes using the second heart sound (S2) information of the patient corresponding to the specified range of contractility determined using the first heart sound (S1) amplitude or energy of the patient.

10. The method of claim 8, wherein the second heart sound (S2) information of the patient includes at least one of a second heart sound (S2) amplitude or energy.

11. The method of claim 7, wherein determining the indication of contractility of the heart includes determining the indication of contractility of the heart for a first cardiac cycle using the first heart sound (S1) amplitude or energy from the first cardiac cycle of the patient, and
wherein determining the blood pressure information of the patient comprises, if the determined indication of contractility of the heart for the first cardiac cycle is within the threshold range, determining blood pressure information of the patient using second heart sound (S2) information from the first cardiac cycle of the patient.

12. The method of claim 11, wherein the threshold range has an upper boundary threshold amount at a median S1 value for the patient.

13. A system, comprising:
a signal receiver circuit configured to receive physiologic information of a patient, including first heart sound (S1) information of the patient and second heart sound (S2) information of the patient, wherein the first heart sound (S1) information includes at least one of a first heart sound (S1) amplitude or energy of the patient; and
an assessment circuit configured to:
determine an indication of contractility of a heart of the patient using at least one of the received first heart sound (S1) amplitude or energy of the patient; and
determine blood pressure information of the patient using the received second heart sound (S2) information of the patient corresponding to a specified range of the determined indication of contractility, the indication of contractility determined using the at least one of the received first heart sound (S1) amplitude or energy of the patient.

14. The system of claim 13, wherein, to determine the blood pressure information of the patient, the assessment circuit is configured to:
if the determined indication of contractility of the heart for a first cardiac cycle is within a threshold range, determine blood pressure information of the patient using the received second heart sound (S2) information for the first cardiac cycle.

15. The system of claim 14, wherein the threshold range has an upper boundary threshold amount at a median S1 value for the patient.

16. The system of claim 13, wherein the second heart sound (S2) information includes at least one of a second heart sound (S2) amplitude or energy, and
wherein, to determine blood pressure information of the patient, the assessment circuit is configured to determine systemic blood pressure information of the patient using the received second heart sound (S2) information of the patient corresponding to the specified range of contractility determined using the received first heart sound (S1) information of the patient.

* * * * *